United States Patent [19]

Malakul

[11] 4,080,247
[45] Mar. 21, 1978

[54] SYSTEM FOR RECYCLING WATER SOLUABLE WASTE LIQUIDS

[76] Inventor: Robert P. Malakul, P.O. Box 865, JFK Airport, New York, N.Y. 11430

[21] Appl. No.: 666,903

[22] Filed: Mar. 15, 1976

[51] Int. Cl.² ............................................. B01D 1/26
[52] U.S. Cl. .................................. 159/17 R; 202/181; 202/176; 202/185 D; 159/28 C
[58] Field of Search ..................... 159/17 R, 28 C, 23, 159/24 A; 203/3, 75, 76, 77; 202/185 D, 174, 235, 181, 176

[56] References Cited

U.S. PATENT DOCUMENTS

| | | | |
|---|---|---|---|
| 2,576,496 | 11/1951 | Ziegler | 159/17 R |
| 3,242,970 | 3/1966 | Schmole | 159/17 R |
| 3,469,616 | 9/1969 | LaGuilharre | 159/17 R |
| 3,527,676 | 9/1970 | Hingst | 159/17 R |
| 3,563,861 | 2/1971 | Fletcher | 159/28 C |

*Primary Examiner*—Hiram H. Bernstein
*Attorney, Agent, or Firm*—John B. Sowell

[57] ABSTRACT

A system for reclaiming solutions of waste chemicals such as ethelene glycol is provided. The water in the ethelene glycol is distilled or evaporated off at temperatures below the boiling point of the glycol. The system includes two or more interconnected evaporating stages each having a heating coil therein. The last or final evaporating stage is provided with an aqueous solution sensing loop for removing portions of reclaimed solution at predetermined concentration levels and is provided with water sensing station for removing condensed steam or returning contaminated water to the input of the system.

11 Claims, 2 Drawing Figures

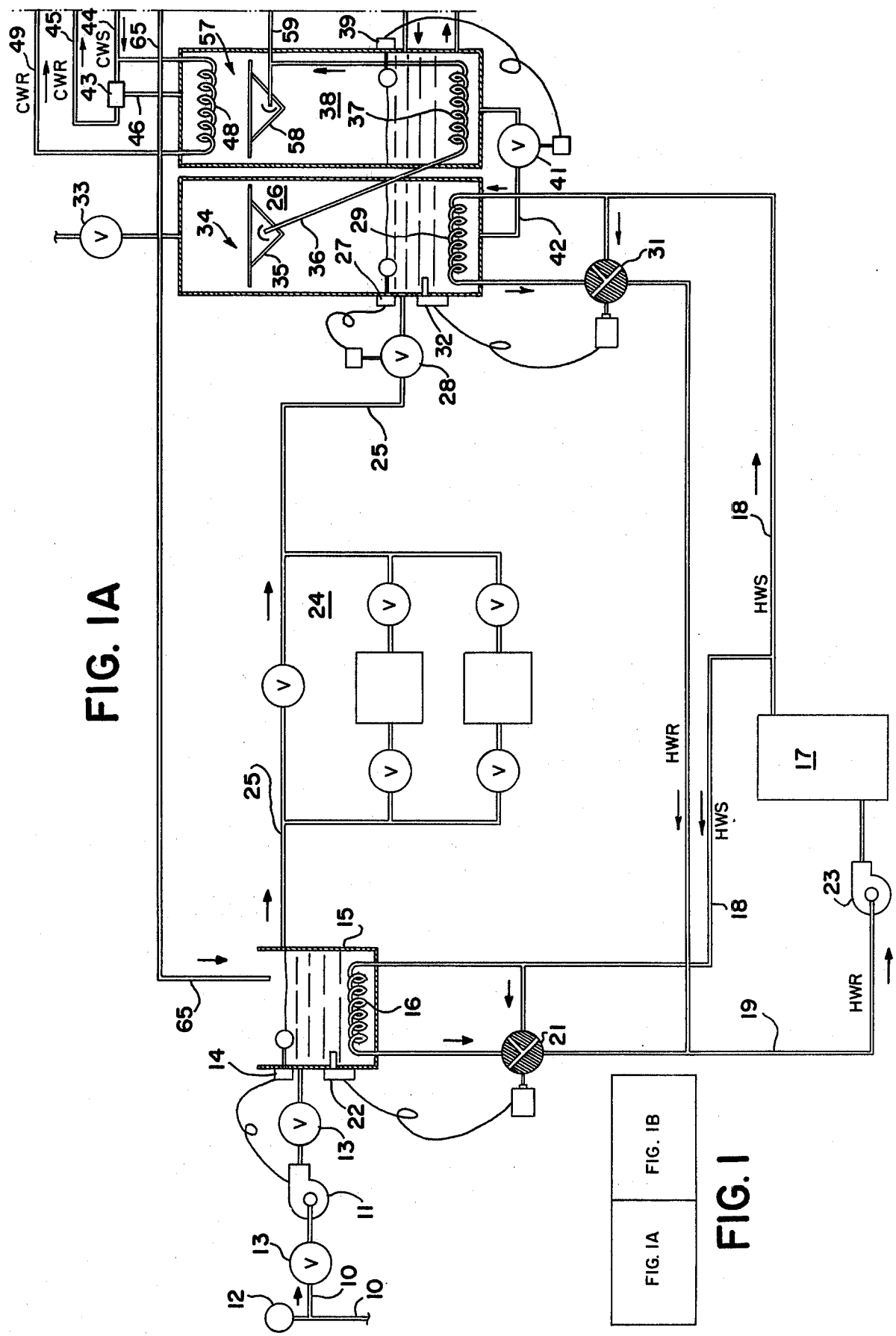

SYSTEM FOR RECYCLING WATER SOLUABLE WASTE LIQUIDS

BACKGROUND OF THE INVENTION

1. Field of the Invention

The present invention relates to a distilling or evaporating system for reclaiming waste ethelene glycol. More particularly, the invention relates to a compact efficient automatic self contain system which is capable of being mounted on a mobil trailer for transportation and use at remote sites.

2. Description of the Prior Art

Distillation systems are well known in the industrial alcohol and petroleum industries. Such systems have reached a very high degree of thermal efficiency and automatic control. These systems are known to be continuous process systems employing numerous sensing controls, elaborate computation equipment and responsive flow control subsystems.

Multiple-effect evaporator systems employing vacuum pressure in the stages are well known in the milk and sugar industries. Such systems seldom exceed four vacuum stages and usually employ the heat of condensed steam in a heating coil in the next higher vacuum stage. The condensed steam leaving a heating coil of a stage is usually dumped in the drainage systems without regard to the degree of contamination carried over into the condensed steam.

It has been estimated that more than twenty-four million gallons of permanent type anti freeze having an ethelene glycol base are used each year in the United States alone. This water soluble oil is dumped by gasoline stations into the sewerage systems of every community in the United States. Large manufacturers using oil and harmful chemicals have been forced by government regulations to remove all types of contaminates from their water before dumping it into a sewage system or into open streams. Large manufacturers employ settling tanks, centrifugal separators and filters to remove contaminates when possible.

Waste chemicals which are in solution and are too weak for commercial use have been refined to remove the pure chemical or to concentrate the chemical solution to a usable strength. Heretofore, systems used to refine waste chemicals have been designed and built as fixed on site systems which are usually large and complex. Seldom are such systems economically justifiable except for very large users of the chemicals being reclaimed.

In the air transportation industry large aircraft are parked in the open between flights. Often the exposed aircraft become covered with cold rain, freezing rain and/or snow. Since the temperature of the atmosphere generally is five degrees fahrenheit colder for every thousand feet of elevation it would be extremely dangerous to allow ice, snow, or moisture covered aircraft to takeoff and rapidly climb to elevations in excess of twenty thousand feet. Not only would ice form on the outer surfaces of the aircraft but the operation of the movable portions of the wings and stablizers and the landing gear would be greatly endangered. It has become standard practice to spray down ice and snow covered aircraft with aqueous solutions of ethelene glycol before takeoff. At J.F. Kennedy International Airport in New York, millions of gallons of ethelene glycol are employed yearly to prepare aircraft for takeoff and no attempt is made to reclaim the waste chemical which has become an environmental problem.

It would be desirable to prevent further environmental damage to the streams, lakes and oceans by the dumping of waste chemicals such as ethelene glycol. Further it would be extremely desirable to provide a reclamation system which was capable of refining and/or reclaiming waste chemicals which not only is economically justifiable, but actually produced recycled usable waste chemicals at a lower cost than new chemicals.

It has always been possible to truck waste chemicals to a recycling plant and to pick up reprocessed chemicals. The problem has been that such plants are few in number and are usually a long distance from the users of the chemical. Further, the recycling plants which are in operation are geared to continuous production and require very large storage facilities. Usually such reclamation systems are not simple enough in basic operation to permit a simple change from one waste chemical to another.

SUMMARY OF THE INVENTION

The present invention provides a small, simple, reliable and self contained portable reclamation system adapted to refine a wide range of aqueous waste chemical solutions.

It is a general object of the present invention to provide an efficient multiple effect evaporation system with a minimum number of sensing controls which are settable to provide continuous automatic operation over a wide range of outputs of chemical concentrations.

It is another principal object of the present invention to provide a simple compact self contained reclamation system which can be trucked to the site of stored waste chemical solutions and to reclaim the stored waste chemicals leaving refined usable concentrated chemicals.

It is another principal object of the present invention to provide a reclamation system capable of being used to reclaim a wide range of waste chemicals.

These and other objects of the present invention are achieved by providing an input solution storage or holding tank into which a portion of the waste solution may be maintained. The solution in the storage tank is continuously supplied to a plural stage multiple effect evaporating system. The final stage of the evaporating system is provided with several new and improved features comprising an aqueous solution sensing loop which recirculates refined solution through the loop until a predetermined concentration of the reclaimed chemical solution is reached and then diverts or bypasses the refined solution to a reclaimed chemical solution storage tank. When the sensing loop determines that the concentration has been reduced below the desired predetermined range, the solution is again recirculated back to the last evaporating stage until the proper concentration is reached. The last evaporating stage is further provided with a novel condensing and steam collecting means which is provided with a water sensing station. The water sensing stations is capable of diverting contaminated condensed steam back to the holding tank and is also capable of diverting substantially pure water to the outlet drain.

DESCRIPTION OF THE PREFERRED EMBODIMENT

Figure 1B:
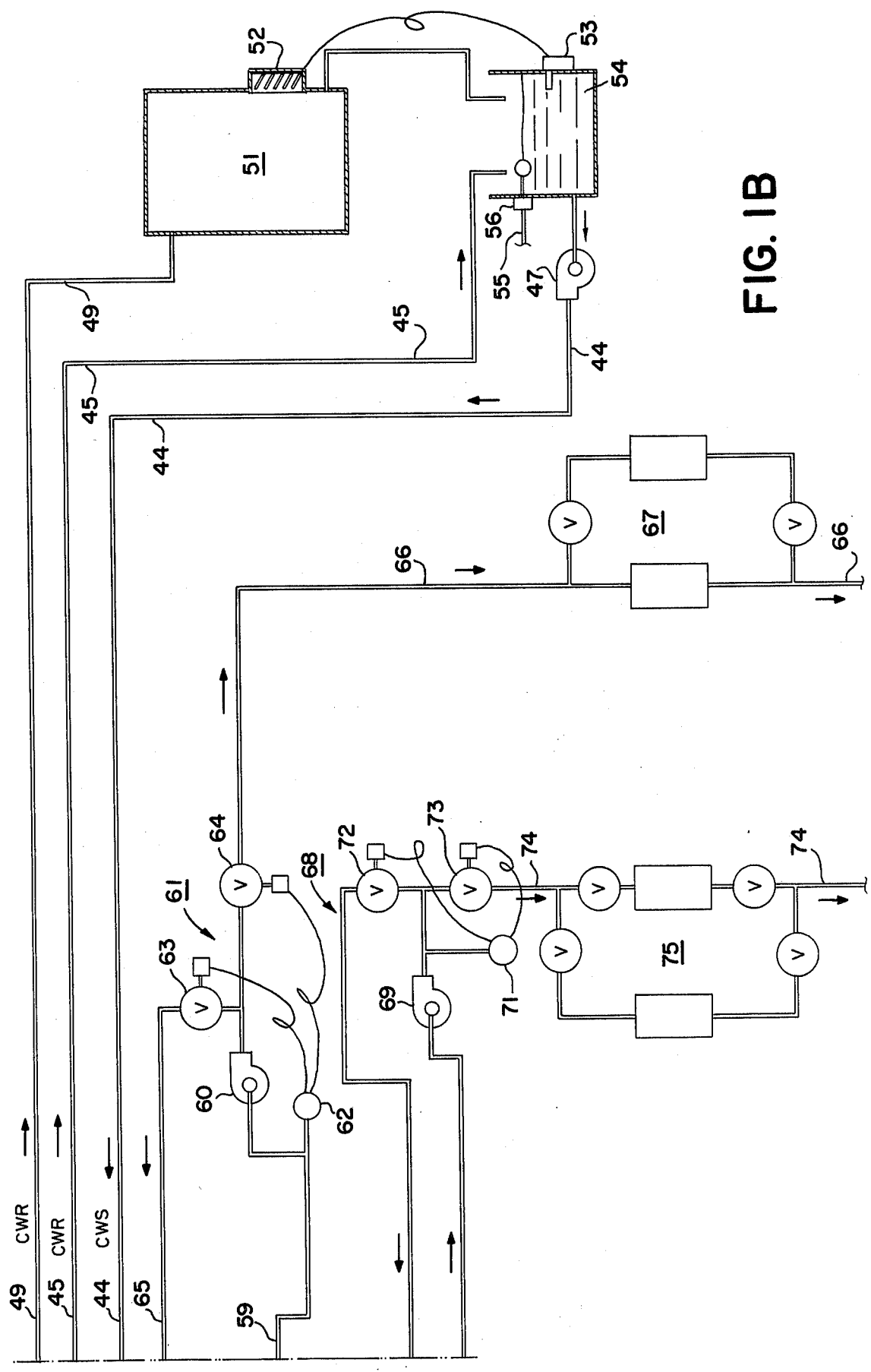
FIG. 1 and 1a are schematic drawings of a multiple-effect evaporating system for conversion of diluted aqueous solutions of ethelene glycol to concentrated usable solutions of ethelene glycol.

Pipe line 10 is a supply line which is connectable to recovery storage tanks located at the site where waste chemical solutions are stored. Feed pump 11 is a preferably gravity fed at the inlet side and is provided with a sensing device 12 in pipe line 10 inlet. Device 12 for ethelene glycol may be a simple density meter. Pump 11, and all equipment in the system which may require repairs, is isolated by valves 13. Addition drain, isolation and check valves are well known and are used throughout the system, but are not shown and discussed as a part of the present system.

Pump 11 is manually controlled or automatically controlled by float control 14 mounted on input solution storage or holding tank 15. The waste chemical solution in tank 15 is preheated to about 110° fahrenheit (°F) by heating coil 16 supplied with hot fluid from hot water heating source 17, The boiler 17 is provided with a hot water (HWS) supply main 18 and a hot water return (HWR) main 19 which are connected to heating coil 16. A three way motor control valve 12 is placed as a shunt bypass across mains 18 and 19 and is controlled by manually settable thermostat 22. The temperature set at thermostat 22 may be varied over a broad range depending on atmospheric temperature, the concentration of the waste solution and the chemical being refined etc. Circulating pump 23 in hot water return main 19 is preferably always on when boiler 17 is in operation providing hot water at or near 180° F for reclamation of ethelene glycol.

Preheated waste chemical solution is piped from tank 15 through an inlet filter bank 24 provided with changable throw away forty micron plated paper filters for removing oil, dirt, grease and other non soluable matter. No pump is shown in supply line 25 because in the preferred embodiment to be explained hereinafter there is a vacuum pressure on line 25. Some waste chemical solutions may require other types of inlet filters or may require no filter, in which case the filter bank 24 may be bypassed or completely eleminated.

The level of preheated waste chemical solution in first evaporating stage 26 is controlled by float control 27 and solenoid valve 28. The temperature of waste chemical solution in first stage tank 26 is maintained at or near 160° F in operation, however, steam is produced at temperatures as low as 140° F by application of proper vacuum pressures. Coil or fluid heating means 29 is connected to the hot water supply 18 and return main 19 which supply 180° F water. Three way motor control valve 31 is placed across mains 18, 19 and is controlled by thermostat 32 to maintain the temperature set at thermostat 32. Saturated steam is produced at 140° F under 2,889 pounds per square inch absolute pressure (5.88 inches mercury). Regulator or vent 33 is provided to purge the system and/or provide additional safety factor.

Steam is produced at first steam collection means 34, shown schematically to include a condensate collection trough 35 and a crossover pipe 36. Crossover pipe 36 is connected to a steam heating coil 37, which serves as a condensing coil for steam and condensate collected in first stage 26.

The level of preheated and concentrated waste chemical solution in second evaporating stage 38 is controlled by float control 39 and solenoid valve 41 in pipe line 42. The temperature of the waste chemical solution is not controlled by a thermostat but is dependent upon several factors including the heat loss to the atmosphere through the tank which comprises the evaporating stages. Saturated steam is produced at 120° F under 1.692 pounds per square inch absolute pressure (3.4458 inches mercury). Eductor 43 is a venture effect vacuum jet capable of producing high vacuum at relative low water pressure supplied at high volume. In the preferred embodiment shown, no control for the vacuum pressure is shown because any additional vacuum supplied merely tends to increase the rate of evaporation of the water from the solution, however, a control valve may be placed in the cold water supply (CWS) line 44 or in cold water return 45. Alternative means of controlling the vacuum at vacuum line 46 may be employed such as bypass lines around eductor 43 or variable speed pump control on water supply pump 47.

Cold water supply 44 is connected to condensing coil 48 and the coil is provided with a separate cold water return 49 which terminates at cooling tower 51. Cooling tower 51 is provided with an internal blower having a set of variable dampers 52 controlled by thermostat 53 in cooling water holding tank 54. Make up water is provided at line 55 which connects to float control valve 56.

It will be understood that eductor 43 pulls or sucks in some steam which is condensed in the cold water supply and returned vai line 45 to tank 54. Cooling tower 51 performs evaporative cooling on the heated cold water return in line 49. Normally there is a need to supply a small amount of make up water which can be supplied from a local source. Should the need for make up water become excessive, the condensed steam may be employed instead of local make up water.

Condensing coil 48 is positioned in the top of second evaporating stage 38 and made large enough to condense substantially all steam being produced in the second stage 38. Second steam collecting means 57 comprises a trough 58 connected to collection pipe 59 which acts as input main to circulating pump 60 of water sensing station 61. Coil 37 connects to main 59. A sensing control 62 in main 59 detects the impurity in the water produced from condensed steam. Ordinarily under ideal operating conditions no impurity or only minor impurity would be detected, however, during fast start up or under excessive heat or vacuum conditions some ethelene glycol can be carried along with the steam. Sensing control 62 may be a sophisticated total carbon analyzer capable of measuring several hundred parts per million of impurity similar to those made by Delta Scientific Inc. of Babylon, L.I. N.Y. or may be a simple electro conductive analyzer.

When the impurity level in the water is low enough to permit discharge into the local drainage system, control 62 opens solenoid valve 63 and closes solenoid valve 64 diverting the water from return pipe 65 to exhaust pipe 66.

Exhaust pipe 66 may be provided with a water filter bank 67 comprising a plurality of replaceable activated charcoal elements which effectively reduce acids and soluable oil waste. When chemicals other than ethelene glycol are being refined, other materials may be substituted.

In a preferred mode of operation, condensed steam from heating coil 37 and condensate collected in trough 58 do not contain undesirable amounts of contaminates and sensing station 61 may not need to be expensive or fully automated, because once the system stablizes the condensate in main 59 may be manually diverted to exhaust pipe 66.

A feature of the present invention is the automatic selectability of a predetermined concentration of refined waste chemical in the solution to be processed regardless of the input concentration. Concentrated waste chemical solution is connected to aqueous solution sensing loop 68 comprising circulating pump 69 and sensing control means 71 in the loop. When controls means 71 senses the range of preset desirable chemical concentration in loop 68 solenoid valve 72 is closed and solenoid valve 73 is opened. At all other times circulating pump recirculates the solution in stage 38 with valve 72 open and valve 73 closed. Sensing control means 71 may be a simple inexpensive density meter with high and low range electrodes for setting a desirable range. A preferred water solution of 40 percent ethelene glycol by volume freezes below −10° F. A 49 percent solution freezes at −30° F and a 52.5 percent solution freezes at −40° F. Ethelene glycol solutions in this range are suitable for use in the aircraft industry for removing snow and ice and can be used by automobiles with the addition of proper relatively inexpensive additives. Substantially pure ethelene glycol can be produced by the present system.

Exhaust pipe 74 may be provided with a filter bank 75 which comprises a plurality of replacable forty micron paper filters. The reclaimed glycol may be dumped in local output storage tanks or pumped to tanks not a part of the present system.

The preferred embodiment reclamation system has been explained with reference to ethelene glycol having a boiling point of 387° F. Chemicals which do not evaporate, vaporize or boil below the temperature of water, may successfully be reclaimed from diluted solution at a much lower cost than the cost of the original chemicals.

In the preferred embodiment system it can be shown that diluted solutions of ethelene glycol as used in the aircraft industry can be reclaimed to useable concentrations at a fraction of the purchase cost of new chemicals. The present system has been mounted on a mobile trailer and can be trucked to a storage site of chemicals where they are reclaimed without the cost of transportation which can make reclamation of diluted waste chemical solution economically prohibitive.

It will be appreciated that a portable system of the type described herein may be employed to refine one chemical and the system purged with clean water and the same system employed to refine a second chemical at a second site. Resetting of the sensing controls or the employment of different and alternative sensing controls may be employed to make a portable system changable without substantial alteration to the automatic reclamation system.

I claim:

1. A system for reclaiming waste chemicals diluted in aqueous solutions comprising:
    a storage tank for storing the waste chemical solution to be refined,
    a first evaporating stage connected to said storage tank for receiving said waste chemical solution,
    first level control means on said first evaporating stage for maintaining a predetermined level of said waste chemical solution therein,
    fluid heating means inside said first evaporating stage for generating low pressure steam from said waste chemical solution,
    first steam and condensate collecting means inside said first evaporating stage,
    a second evaporating stage containing waste chemical solution and having a steam heating coil therein connected to said first steam and condensate collecting means,
    second steam and condensate collection means inside said second evaporating stage,
    said second steam and condensate collection means being connected to said steam heating coil inside said second evaporating stage,
    condensing coil means inside said second evaporating stage for condensing steam generated in said second evaporating stage,
    liquid conduit means connecting the aqueous solutions in said first and said second evaporating stages,
    second level control means on said second evaporating stage for opening and closing said liquid conduit means to maintain a predetermined level of said waste chemical solution in said second evaporating stage,
    vacuum means connected to said second evaporating stage for reducing the pressure in said second evaporating stage below atmospheric pressure,
    an aqueous solution sensing loop having an inlet and an outlet connected to the waste chemical solution in said second evaporating stage, said aqueous solution sensing loop comprising a liquid circulating pump, bypass valve control means and sensing control means for determining the amount of waste chemical in the solution being pumped in said sensing loop, a water sensing station connected to said second steam and condensate collection means, said water sensing station comprising, a liquid circulating pump, diversion valve control means and a purity sensing control for determining the amount of chemical impurity in the condensed steam being pumped in said water sensing station and
    collection storage means connected to said by pass valve control means for receiving portions of said waste chemical solution from said second evaporating stage when a predetermined concentration of waste chemical is sensed by said sensing control means, whereby reclaimed waste chemical is intermittently provided at said collection storage means.

2. A system as set forth in claim 1 which further includes, a return pipe connected to said water sensing station and to said storage tank for returning condensed steam to said storage tank when the condensed steam contains excessive impurity as determined by said sensing control.

3. A system as set forth in claim 2 which further includes,
    an exhaust pipe connected to said water sensing station and to an outlet drain for exhausting condensed steam when the condensed steam contains only a predetermined allowable impurity as determined by said sensing control.

4. A system as set forth in claim 3 which further includes,
    manual control means on said purity sensing control for selecting said return pipe or said exhaust pipe.

5. A system as set forth in claim 3 which further includes,
a water filter bank connected to said exhaust pipe for removing chemical impurities from said condensed steam.

6. A system as set forth in claim 1 wherein said waste chemical solution comprises an aqueous solution of ethelene glycol, and said system further includes,
a hot fluid supply connected to said heating means in said first evaporating stage,
temperature control means in said hot fluid supply, and
a thermostat control in said first evaporating stage for controlling the supply of hot fluid to said heating means.

7. A system as set forth in claim 6 wherein said thermostat control maintains said ethelene glycol solution at a temperature of approximately 160° fahrenheit and said vacuum means connected to said second evaporating stage pulls a vacuum in said first evaporating stage through said heating coil and said first steam collecting means sufficient to produce steam and condensate in said first evaporating stage at approximately 140° fahrenheit.

8. A system as set forth in claim 6 wherein said vacuum means pulls a vacuum in said second evaporating stage sufficient to produce steam in said second evaporating stage at approximately 120° fahrenheit.

9. A system as set forth in claim 6 wherein said hot fluid supply is further connected to a heating coil in said storage tank for preheating said waste chemical solution of ethelene glycol.

10. A system as set forth in claim 9 wherein said preheated solution of ethelene glycol is filtered before being connected to said first evaporating stage.

11. A system as set forth in claim 1 wherein said waste chemical solution comprises an aqueous solution of ethelene glycol, and said system further includes,
a filter bank connected to by pass control means between said collection storage means for filtering and aqueous solution of ethelene glycol, and
wherein said sensing control means are set to bypass an approximate 50 percent by volume filtered solution of ethelene glycol to said collection storage means.

* * * * *